(12) United States Patent
Perrone (10) Patent No.: US 9,057,667 B2
(45) Date of Patent: Jun. 16, 2015

(54) DEVICE AND METHOD FOR TESTING PRESSURE OF HYDRAULIC TOOLS

(71) Applicant: Michael Perrone, Seaford, NY (US)

(72) Inventor: Michael Perrone, Seaford, NY (US)

( * ) Notice: Subject to any disclaimer, the term of this patent is extended or adjusted under 35 U.S.C. 154(b) by 251 days.

(21) Appl. No.: 13/931,893

(22) Filed: Jun. 29, 2013

(65) Prior Publication Data

US 2014/0157885 A1 Jun. 12, 2014

Related U.S. Application Data

(60) Provisional application No. 61/665,918, filed on Jun. 29, 2012, provisional application No. 61/745,555, filed on Dec. 22, 2012.

(51) Int. Cl.
*G01N 3/08* (2006.01)
*G01M 99/00* (2011.01)
*A62B 3/00* (2006.01)

(52) U.S. Cl.
CPC ............... *G01N 3/08* (2013.01); *G01M 99/007* (2013.01); *A62B 3/005* (2013.01)

(58) Field of Classification Search
None
See application file for complete search history.

(56) References Cited

U.S. PATENT DOCUMENTS

| | | | | | |
|---|---|---|---|---|---|
| 4,137,757 | A | * | 2/1979 | Kovacs | 73/860 |
| 4,241,795 | A | * | 12/1980 | Landry, Jr. | 173/90 |
| 4,960,265 | A | * | 10/1990 | Nichols | 254/93 R |
| 5,237,613 | A | * | 8/1993 | Berry et al. | 60/632 |
| 5,343,752 | A | | 9/1994 | Woyski et al. | |
| 5,428,853 | A | * | 7/1995 | Menke et al. | 7/138 |
| 5,665,919 | A | | 9/1997 | Woyski et al. | |
| 6,318,228 | B1 | * | 11/2001 | Thompson | 89/1.14 |
| 8,046,908 | B2 | | 11/2011 | Shinjo | |
| 2002/0005609 | A1 | | 1/2002 | Mattox et al. | |
| 2002/0162400 | A1 | | 11/2002 | Xie et al. | |
| 2004/0177662 | A1 | * | 9/2004 | Bosse | 70/465 |

FOREIGN PATENT DOCUMENTS

GB 2480083 A * 11/2011

OTHER PUBLICATIONS

International Search Report and Written Opinion of the ISA, dated Oct. 14, 2013, for counterpart PCT application PCT/US2013/048831.

* cited by examiner

*Primary Examiner* — Andre Allen (57) ABSTRACT

Devices and methods are provided for testing and maintaining hydraulic tools and, in particular, devices and methods for testing and maintaining hydraulic forcible entry tools that are used to forcibly open locked doors, for example, in emergency situations.

9 Claims, 12 Drawing Sheets

DEVICE AND METHOD FOR TESTING PRESSURE OF HYDRAULIC TOOLS

CROSS-REFERENCE TO RELATED APPLICATION

This application claims priority to U.S. Provisional Patent Application No. 61/665,918, filed on Jun. 29, 2012, and to U.S. Provisional Patent Application No. 61/745,555, filed on Dec. 22, 2012, the disclosures of which are incorporated herein by reference.

TECHNICAL FIELD

The field generally to devices and methods for testing and maintaining hydraulic tools and, in particular, devices and methods for testing and maintaining hydraulic forcible entry tools that are used to forcibly open locked doors, for example, in emergency situations.

BACKGROUND

In emergency situations, police, firefighters, and other first responders may need to forcibly enter a building or dwelling to gain access in order to save lives. One common method of forcible entry in forcibly opening a locked door. In general, emergency personnel and first responders typically rely on a number of different devices to force entry through a locked door into a dwelling or building. Prying tools, such as "Halligan" tools and crowbars are common tools used to breach doors and windows. A Halligan is a special tool commonly used by firefighters for prying, twisting, punching, or striking.

Other tools that are commonly used to forcible open locked doors are generally referred to as "hydraulic forcible entry tools". These tools are generally designed to forcibly open locked doors that open inwardly (right or left handed inwardly swinging doors), as well as forcibly open other types of non-hinged doors such as elevator doors that can be spread apart. There are various commercially available hydraulic forcible entry tools. Currently, the most commonly used commercially available hydraulic forcible entry tools are known as the "HYDRA RAM" and the "RABBIT TOOL." These hydraulic forcible entry tools are shown in FIGS. 1A, 1B and 2.

Figure 1A:
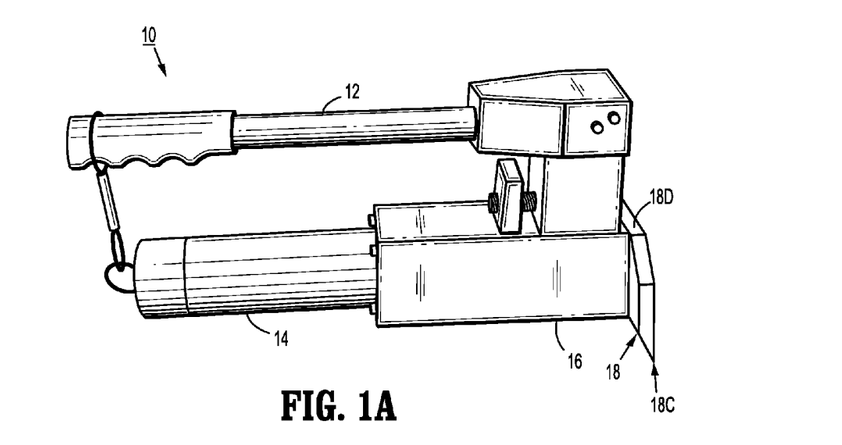
FIGS. 1A and 1B illustrate one type of hydraulic forcible entry tool.
Figure 1B:
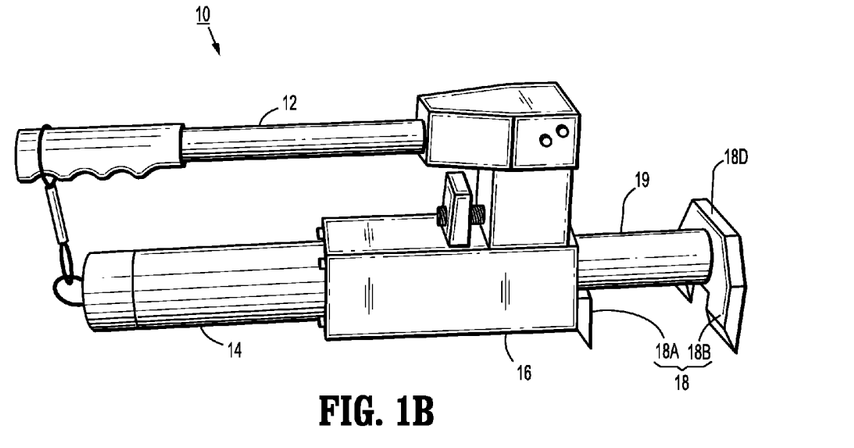
Figure 2:
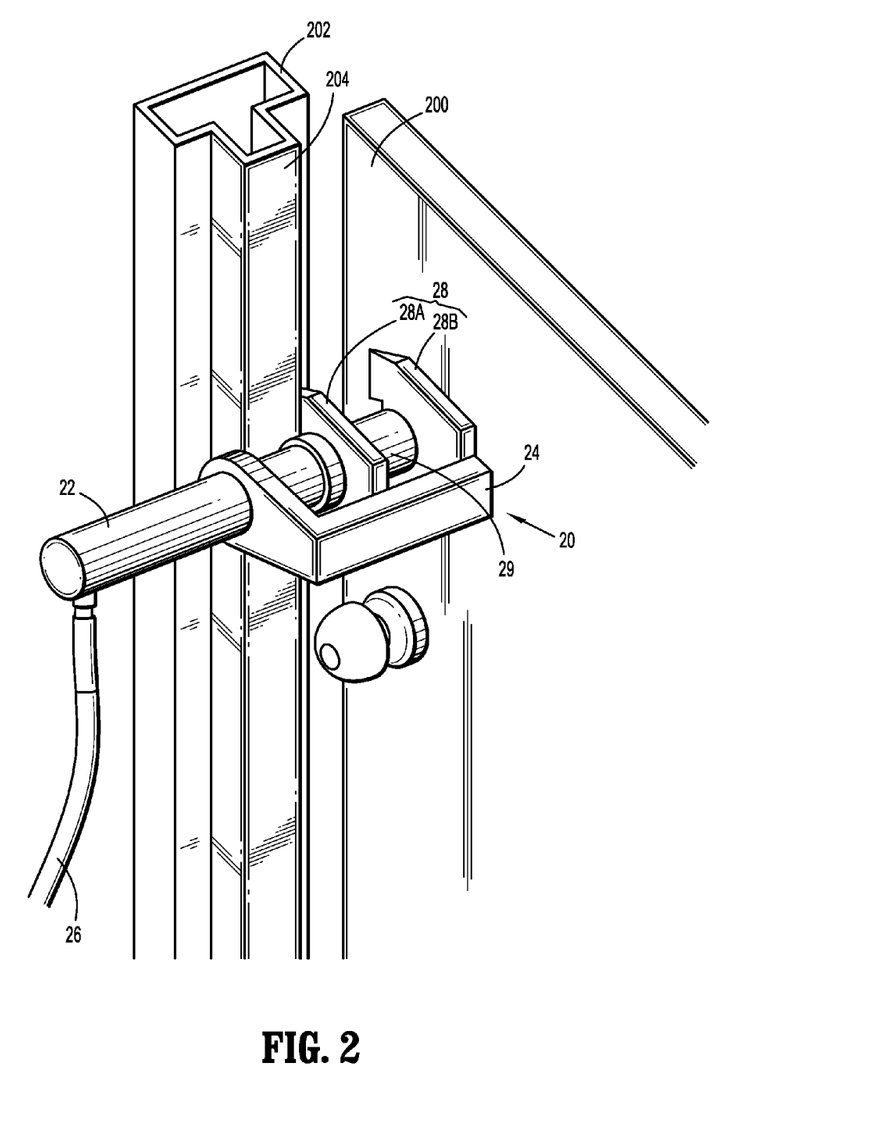
FIG. 2 illustrates another type of hydraulic forcible entry tool and its use in forcibly opening an inward swinging door.

In particular, FIGS. 1A and 1B illustrate a hydraulic forcible entry tool (10) that is sold under the name brand "HYDRA RAM." The hydraulic forcible entry tool (10) comprises a first handle (12), a second handle (14), a hydraulic, housing (16), spreading jaws (18), and a movable piston (19). As further shown in FIG. 1B, the spreading jaws (18) include a fixed jaw member (18A) that is connected to the hydraulic, housing (16), and a movable jaw member (18B) that is connected to an end of the movable piston (19). FIG. 1A illustrates the hydraulic forcible entry tool (10) in a non-extended position wherein the piston (19) is retracted into the hydraulic housing (16) and wherein the fixed and movable jaws (18A) and (18B) are joined together forming a sharp blade tip (18C). FIG. 1B illustrates the hydraulic forcible entry tool (10) in an extended position wherein the piston is extended out from the hydraulic housing (16) and wherein the fixed and movable jaws (18A) and (18B) are separated.

In operation, starting from the non-extended position shown in FIG. 1A, the hydraulic forcible entry tool (10) would be positioned at some point of the door where a door lock (e.g., dead bolt, door handle, etc.) exists, with the sharp edge (18C) of the jaws (18) forcibly inserted between the door and a door stop. In this position, the bottom of the hydraulic housing (16) would rest against the door stop/frame (parallel with the door frame) and the outer surface of the movable jaw (18B) would be pushed up flat against the surface of the door.

The individual using the tool (10), holding both handles (14) and (12), would start pumping the movable handle (12) back and forth to operate a hydraulic pump within the housing (16), causing the piston (19) to extend out from the housing (16). With the fixed jaw (18A) pressing against the inner surface of the door stop and the movable jaw (18B) pressing against the door, the door is forcibly pushed open as the piston (19) extends further out until the door is forcibly pushed open by, e.g., breaking the lock. A hydraulic forcible entry tool (10) as shown in FIGS. 1A and 1B sold under the name brand of "HYDRA RAM" provides a jaw spread of 4 to 6 inches (extension of piston (19)) with a rated maximum spreading force of 10,000 psi.

Moreover, FIG. 2 illustrates another type of hydraulic forcible entry tool (20) that is known as the "RABBIT TOOL." FIG. 2 shows the hydraulic forcible entry tool (20) in operation, forcibly opening an inwardly swinging door (200). The hydraulic forcible entry tool (20) comprises a handle/hydraulic housing unit (22), a high-pressure hose (26) connected to a pump not shown), spreading jaws (28), a slidable bracket/guide (24) and a movable piston (29). The spreading jaws (28) include a fixed jaw member (28A) that is connected to the housing (22) and a movable jaw member (28B) that is connected to an end of the movable piston (29).

The operation of the hydraulic forcible entry tool (20) is similar to that discussed above for the hydraulic forcible entry tool (10) of FIGS. 1A and 1B. More specifically, in operation, starting from the non-extended position, the hydraulic forcible entity tool (20) would be pushed against the door (200) and a door frame (202) at some point of the door (200) where a door lock (e.g., dead bolt, door handle, etc.) exists, with the sharp edge of the jaws (28) forcibly inserted between the door (200) and a door stop (204). The individual using the hydraulic forcible entry tool (20) would hold the tool (20) in position against the door (200) and door frame (202), and the pump apparatus (not shown) would be started to cause hydraulic fluid to be pumped through the hose (26) into the housing (22) causing the piston (29) to movably extend out from the housing (22). As shown in FIG. 2, with the fixed jaw (28A) pressing against the inner surface of the door stop (204) and the movable jaw (28B) pressing against the door (200), the door (200) is forcibly pushed away from the door stop (204) as the piston (29) is extended until the lock(s) is/are broken.

In order to ensure proper operation of a hydraulic forcible entry tool such as described above, it is important to inspect and maintain the tool on a frequent basis. The inspection and maintenance of hydraulic forcible entry tools on a routine basis (e.g., weekly) is vital to ensuring that the tools are battle ready and will not fail when they are used in an emergency situation. One way to properly inspect and maintain a hydraulic forcible entry tool is to frequently test the tool under a "load". Testing a hydraulic forcible entry tool under a "load" serves various purposes.

For example, operating a hydraulic forcible entry tool under a "load" forces the oil to properly lubricate the internal hydraulic gaskets. Failures are common in hydraulic forcible entry tools that have sat around for long periods of time without use, causing the internal seals to dry out and crack, and therefore leading to possible failure. Some individuals attempt to test and maintain a hydraulic forcible entry tool by simply pumping the tool and extending the piston under no tension or load, and then retracting the piston. However, this operation does not adequately force the oil up into the internal gaskets to keep them lubricated and moist and prevent the internal gaskets/seals from cracking. When the internal seals in the hydraulic tool dry out, they tend to crack and become brittle over time, which weakens the seals and results in tool failure when used under a load.

Furthermore, operating a hydraulic forcible entry tool under a "load" ensures that the tool will actually work properly and not fail under load conditions. Indeed, even if the tool appears to work properly when the tool is operated without a load (i.e., the piston extends out when the tool is pumped), the tool can still result in a failure and not be able provide sufficient spreading force when used in an emergency condition under a load.

Currently, there are no known devices that provide controlled load conditions for testing and maintaining hydraulic forcible entry tools. To check a hydraulic forcible entry tool under "load" conditions, some individuals will place the jaws of the tool between the open jaws of a bench vise grip and then operate the hydraulic forcible entry tool until the jaws of the hydraulic forcible entry tool press against the jaws of the bench vise grip. Other individuals may operate the hydraulic forcible entry tool by lifting, objects such as dumpsters, soda machines, or other heavy objects. However, testing and maintain a hydraulic forcible entry tool using these raw techniques can be problematic for various reasons.

For example, operating hydraulic forcible entry tool in a vise grip or using the tool to lift heaving objects can over exert the tool, putting great stress on the tool and damaging the tool's inner seals in ways that can lead to subsequent premature failures. Moreover, these raw test methods do not allow an individual to determine with any reasonable degree of certainty the amount of pressure (psi) that the tool is actually providing at the time of testing. Indeed, even if the hydraulic forcible entry tool docs seem to function properly under a given load (e.g., vise grips or lifting an object), the individual testing the tool has no way of determining how much force the tool is providing under the given load. In this instance, even if a hydraulic forcible entry tool is capable of providing some spreading force under an unknown load, the tool may still be in a current state in which it is incapable of providing sufficient spreading force to operate the tool in its intended manner, such as forcibly opening a steel door with dead bolts.

SUMMARY

Embodiments of the invention generally include devices and methods for testing and maintaining hydraulic tools and, in particular, devices and methods for testing and maintaining hydraulic forcible entry tools that are used to forcibly open locked doors, for example.

In one embodiment of the invention, a device for testing a hydraulic tool includes a support base a first fixed plate fixedly connected to the support base, a second fixed plate fixedly connected to the support base, a movable plate, disposed between the first and second fixed plate, and one or more compression springs disposed between the movable plate and the second fixed plate. The movable plate and the first fixed plate are oriented with respect to each other and adapted to engage a hydraulic tool being tested. The movable plate is adapted to be moved towards the second fixed plate upon actuation of the hydraulic tool and compress the one or more compression springs to provide a compression force that provides a test load for testing the hydraulic tool.

These and other embodiments of the present invention will become apparent from the following detailed description of embodiments, which is to be read in conjunction with the accompanying figures.

DETAILED DESCRIPTION OF EMBODIMENTS

In general, devices and methods for testing and maintaining hydraulic tools in accordance with exemplary embodiments of the invention will now be discussed in further detail with references to FIGS. 3A, 3B, 4A and 4B. The exemplary test devices and methods discussed herein can be used for testing and maintaining a hydraulic forcible entry tools such as discussed above with reference to FIGS. 1A, 1B, and FIG. 2.

Figure 3A:
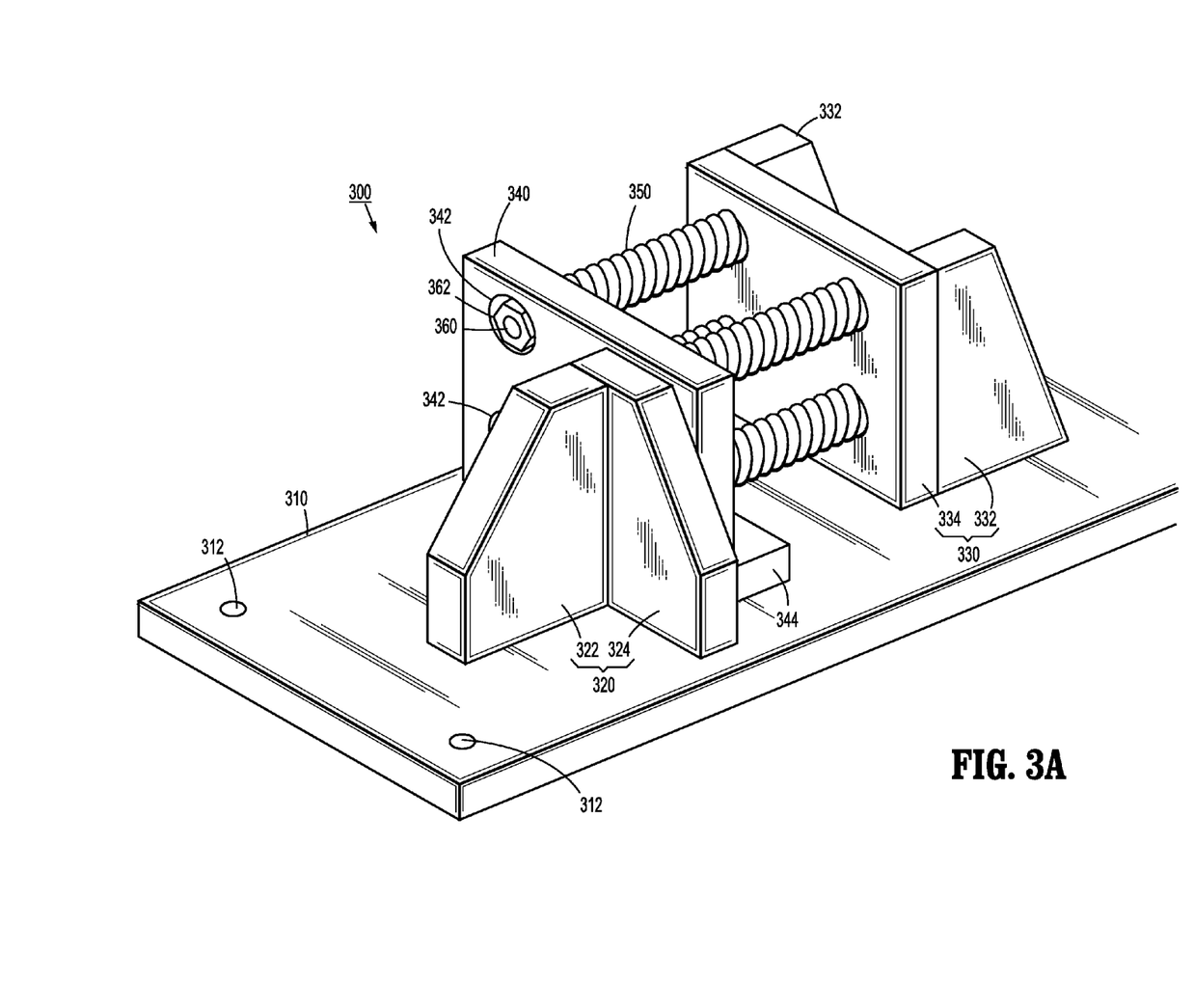
FIGS. 3A and 3B are schematic perspective views of a device for testing and maintaining a hydraulic tool, according to an exemplary embodiment of the invention.
Figure 3B:
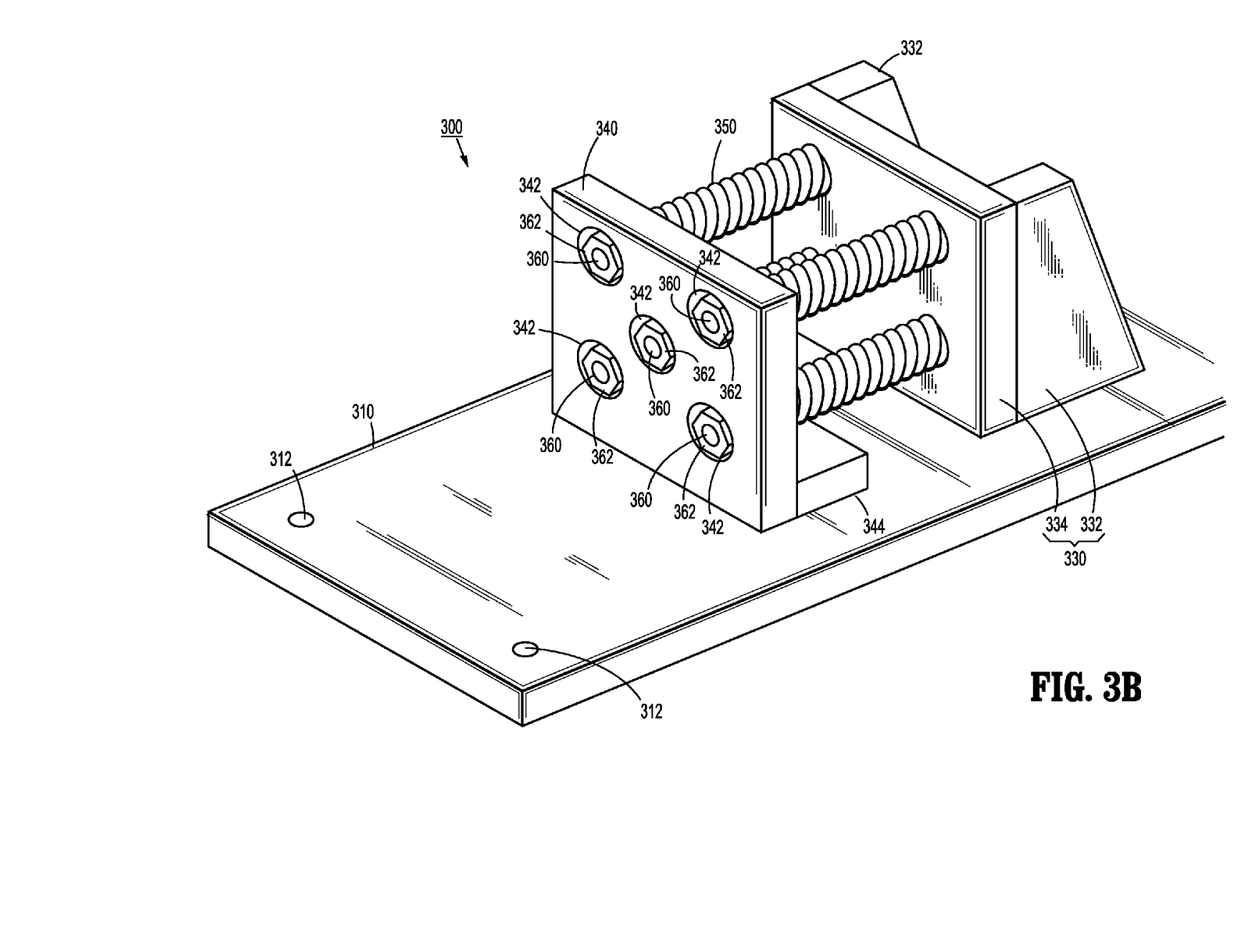

FIGS. 3A and 3B are schematic perspective views of a test device (300) for testing and maintaining a hydraulic tool, according to an exemplary embodiment of the invention. As shown in FIGS. 3A and 3B, the test device (300) generally includes a support base (310), a first fixed plate (320), a second fixed plate (330), a movable plate (340), and as plurality of springs (350) disposed between the movable plate (340) and the second fixed plate (320). The first fixed plate (320) comprises a first member (322) and a second member (324) which form a right angle (90 degrees) fixed plate structure. The second fixed plate (330) comprises a first member (334) that is disposed parallel to the movable plate (340), and a plurality of extended support members (332) that are disposed perpendicular to the first member (334) to provide support for compressive forces that are applied to the second fixed plate (330), as will be described below.

In one embodiment of the invention, the support base (310), first fixed plate (320), second fixed plate (330), and a movable plate (340) are made of a metallic material such as ⅜ inch or ½ inch thick steel, for example. The constituent components (322) and (324) of the first fixed plate (320) may be separate elements that are welded together to form the first fixed plate (320). Similarly, the constituent components (332) and (334) of the second fixed plate (330) may be welded together to form the second fixed plate (330). The first fixed plate (320) and the second fixed plate (330) may be welded to the supporting base plate (310). The supporting base plate (310) may comprise a plurality of thru-holes (312) formed in corner regions of the base plate (310) so that the test device (300 can be bolted or screwed down to a supporting work bench structure, for example.

In one exemplary embodiment as shown in FIGS. 3A and 3B, a bolt (360) longitudinally extends within the interior of each spring (350) and passes through corresponding holes formed in the movable plate (340) and the flat plate portion (334) of the second fixed plate (330). In the exemplary embodiment shown in FIGS. 3A and 3B, a nut (362) is screwed on to each threaded end of the bolts (360). A plurality of recesses (342) are formed on one surface of the movable plate (340) to a depth sufficient to recess the nuts (362).

The nuts (362) on the threaded ends of the bolts (360) that pass through the movable plate (340) are preferably tack welded in place within the recesses (342) so that the nuts (362) and ends of the bolts (360) are fixedly connected to each other and fixedly connected to the movable plate (340). The nuts (362) on the other threaded ends of the bolts (360) that pass through holes formed in the flat plate portion (334) of the second fixed plate (330) are tack welded to each other, but not to the flat plate portion (334) of the second fixed plate (330). Indeed, while one end of the threaded bolts (360) are fixedly connected to the movable plate (340), the other end of the threaded bolts (360) can slidably move back and forth through holes formed in the second fixed plate (330) while the test device (300) is being used (as further explained below).

In the exemplary embodiment of FIGS. 3A and 3B, the test device (300) is shown to have 5 springs (350) disposed and symmetrically arranged between the movable plate (340) and the flat plate (334) of the second fixed plate (330), although any number and arrangement of springs may be employed depending on the application. The springs (350) an be any type of compression coil spring (helical or conical coil springs, for example) that exert an opposing force against the movable, plate (340) as the springs (350) are compressed from the movable plate (340) being pushed towards the second fixed plate (330) when testing a hydraulic tool using the test device (300), as will be explained, in further detail below. The exemplary embodiment of FIGS. 3A and 3B illustrates the use of engine valve springs having threaded rods that pass through the center of the valve springs. Other types of commercially available or special manufactured compression springs may be employed in a test device according to other embodiments of the invention.

Each spring (350) exerts a maximum compression force, so the number of compression springs used will vary depending on the maximum amount of test force that the test device is designed for. In general, the opposing force F exerted by a compression spring as it is compressed can be determined from Hooke's Law: $F=k(L_{free}-L_{def})$, where k is the spring constant or force constant of the spring (a constant that depends on the spring's material and construction), $L_{free}$ is the spring free length, i.e., the length of the compression spring when uncompressed, and where $L_{def}$ is the length of the compression spring in a compressed state. In this regard, the force with which a compression spring pushes back is proportional to the distance from its free (equilibrium) length.

In the exemplary embodiment of FIGS. 3A and 3B, for example, assuming that each of the 5 springs (350) is rated to provide 2000 PSI of maximum compression force, the use of the 5 springs (350) in parallel between the moving plate (340) and the second fixed plate (330) can provide a maximum rating of about 10,000 psi of test force for testing the spreading force of a hydraulic forcible entry tool, such as discussed above with reference to FIGS. 1A/1B and 2.

Figure 4A:
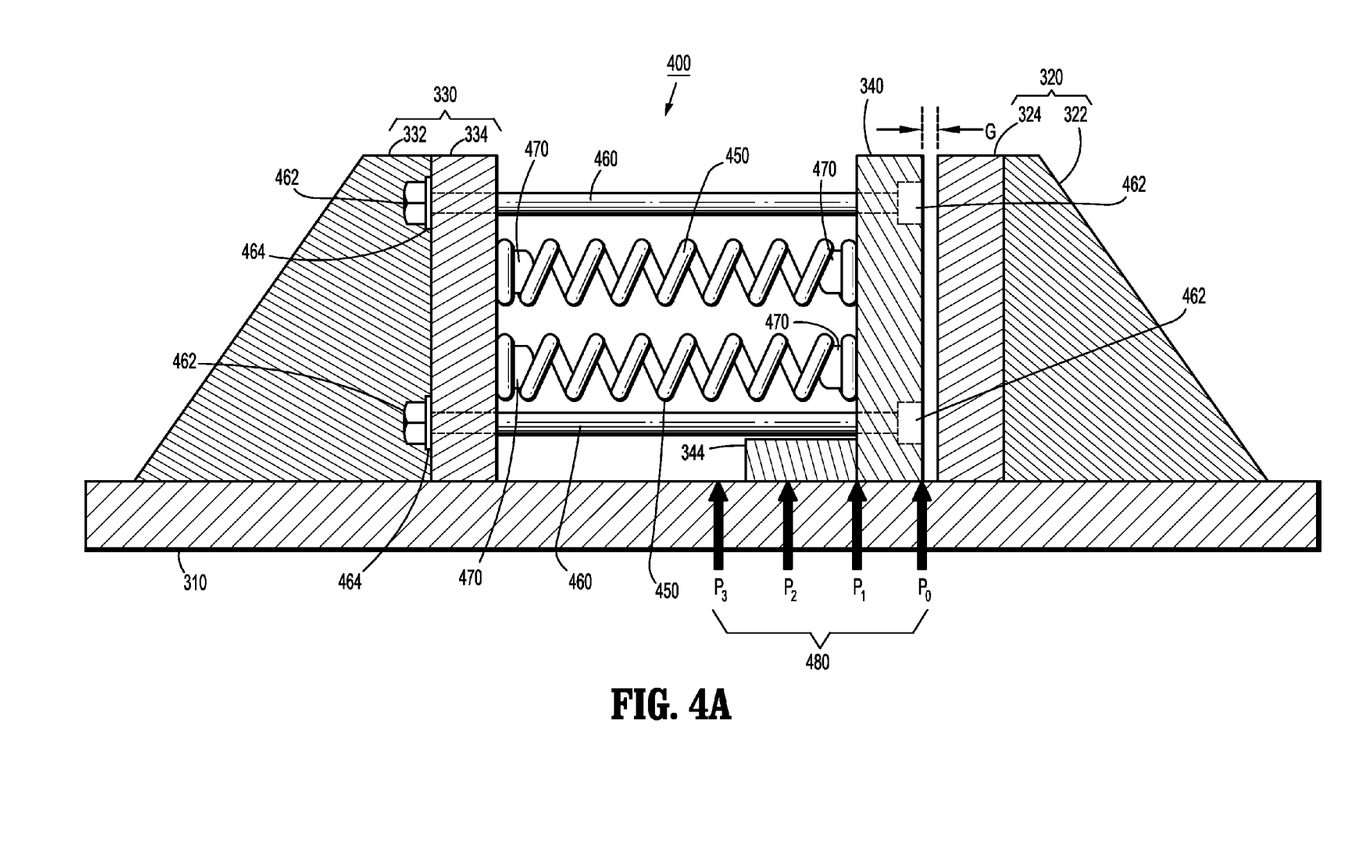
FIGS. 4A and 4B are side schematic views of a device for testing and maintaining a hydraulic tool, according to another exemplary embodiment of the invention.
Figure 4B:
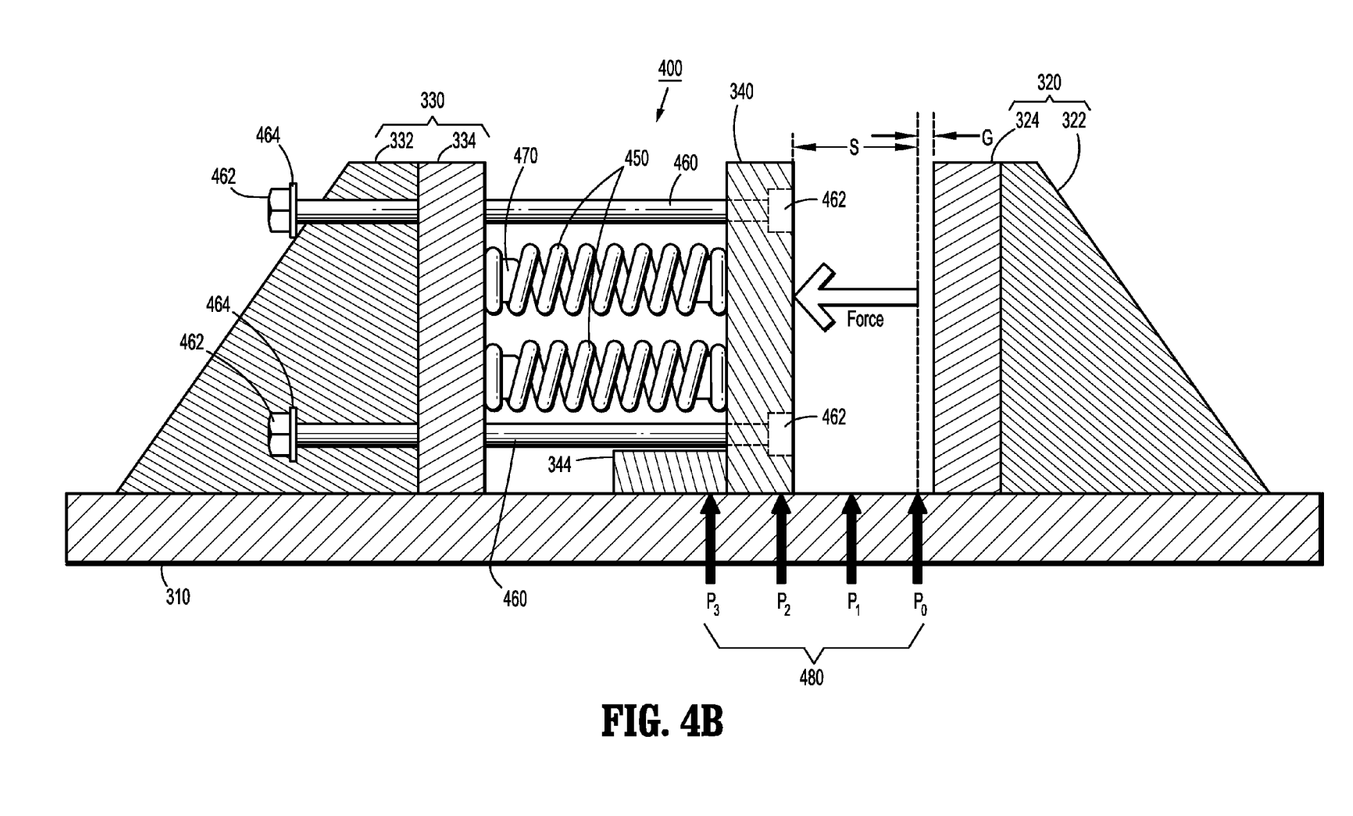

FIGS. 4A and 4B are side schematic views of a device for testing and maintaining a hydraulic, tool, according to another exemplary embodiment of the invention. In particular, FIGS. 4A and 4B illustrate a test device (400) for testing and maintaining a hydraulic tool, which is similar to the test device (300) of FIGS. 3A/3B in that the test device (400) includes a support base (310), a first fixed plate (320), a second fixed plate (330), a movable plate (340), and a plurality of springs (450) disposed between the movable plate (340) and the second fixed plate (320).

The test device (400) differs from the test device (300) of FIGS. 3A/3B in that the test device (400) of FIGS. 4A/4B comprises a plurality of springs (450) and a plurality of bolts (or rods) (460) that are separate from each other (the bolts are not disposed within the interior of the springs). The springs (450) are held in place between the movable plate (340) and the flat plate portion (334) of the second fixed plate (330) using a plurality of metallic studs (470) that are fixedly connected (e.g., welded) to facing surfaces of the movable plate (340) and the that plate portion (334) of the second fixed plate (330). The studs (470) are dimensioned (having a diameter) to snuggly fit within the inner region (inner diameter) of the compression springs (450).

The bolts (460) pass through corresponding holes formed in the movable plate (340) and the flat plate portion (334) of the second fixed plate (330). A nut (462) is screwed on to each threaded end of the bolts (460). A plurality of recesses are formed on one surface of the movable plate (340) to a depth sufficient to recess the nuts (462). The nuts (462) on the threaded ends of the bolts (460) that pass through the movable plate (340) are preferably tack welded in place within the recesses so that the nuts (462) and ends of the bolts (460) are fixedly connected to each other and to the movable plate (340). The nuts (462) on the other threaded ends of the bolts (460) that pass through holes Rimed in the flat plate portion (334) of the second fixed plate (330) are tack welded to each other, but not to the flat plate portion (334) of the second fixed plate (330). This allows the bolts (460) to slidably move back and forth through the holes formed in the second fixed plate (330) While the test device (300) is being used (as shown in FIG. 4B). A washer (464) may be used on the ends of the bolts (460).

The operation of the test device (300) of FIGS. 3A and 3B and the test device (400) of FIGS. 4A and 4B are the same, and will now be further discussed with primary reference to FIGS. 4A and 4B. In each of the exemplary test device embodiments discussed herein, the initial distance between the movable plate (340) and the flat plate portion (334) of the second fixed plate (330) depends, for example, on the spring free length $L_{free}$ (length of compression spring when uncompressed) of the compression springs 350, 450 that are employed.

As specifically shown in FIG. 4A, the first fixed plate (320) is fixedly connected to the support plate (310) such that a small gap G (space) exists between the movable plate (340) and the second member (324) of the first fixed plate (320) when the springs (450) are in an uncompressed state (i.e., no force is applied to the surface of the movable plate (340)). The small gap G can be in a range of about ⅛ inch to ¼ inch, or any other suitable distance, that would sufficient to insert the tip of the (non-extended) spreading jaws or blades of a hydraulic forcible entry tool into the gap G when testing the hydraulic tool. In some embodiments, the initial gap G can be adjusted by turning the nuts (462) on the threaded end of the rods (460) to increase or decrease the distance between the plate elements (334) and (340).

By way of example, starting with the hydraulic forcible entry tool (10) of FIG. 1A in a non-extended position, the sharp blade tip (18C) of the joined fixed and movable jaws (18A) and (18B) would be inserted into the gap G between the movable plate (340) and the first fixed plate (320). The hydraulic forcible entry tool (10) would be oriented with the bottom surface of the hydraulic housing (16) resting, against the surface of the first member (322) of the first fixed plate (322) and with the outer surface of the movable jaw (18B) pushed up flat against the surface of the movable plate (340). In this regard, the first fixed support plate (320) of the test device would emulate a doorframe and the movable plate (340) would emulate a door to be forcibly pushed open.

Once in this initial position, the hydraulic forcible entry tool (10) would be operated by pumping the movable handle (12) back and forth to cause the piston (19) to movably extend out from the housing (16). With the fixed jaw (18A) held pressing, against the first fixed support plate (320) and the movable jaw (18B) pressing against the movable plate (340) the tool (10) would be operated to extend the piston (19) and start exerting a force F against the movable plate (340), as shown in FIG. 4B, causing the compression springs (450) to compress as the movable plate (340) is pushed towards the second fixed plate (330).

As further shown in FIG. 4B, once the movable plate (340) is pushed towards the second fixed plate (330) the end portions of the bolts (460) slidably pass through holes formed in the flat plate portion (334) and movably extend out behind, the second fixed support plate (330). In one exemplary embodiment, a shown in FIGS. 3A/3B and 4A/4B a lower plate element (344) may be connected welded) to the bottom of the movable plate (340). This lower plate element (344) serves several purposes. For instance, the lower plate (344) can serve as a means to stabilize the movable plate (340) as it slides back and forth. Moreover, the lower plate (344) can serve as a stop element to limit the amount of distance that the movable plate (340) can be pushed towards the inner surface of the element (334) of the second fixed plate (330) (so as to not over exert the compression springs (450)).

Referring again to FIG. 4B, as the movable plate (340) is pushed towards the second fixed plate (330) with an increasing spreading distance, "S", from the initial gap G point, more force F is needed to further compress the springs (450). This spreading distance "S" is equal to the decrease in the length of each compression spring (450) from their initial spring free length, $L_{free}$ (length of the compression spring (450) when uncompressed), to a decreased length, $L_{def}$ (the length of compression springs (450) at a given compressed state). Based on the equation of Hooke's Law as discussed above, this amount of spreading distance S is substantially proportional to the amount of force exerted by each compression spring (450), wherein a total of the compression forces applied by the compression springs (450) will be substantially equal to the amount of force applied by the hydraulic tool (10) when the movable jaw is extended at a given spreading distance S.

To determine an amount of spreading force that a given hydraulic tool is providing while being tested using the test devices (300) or (400) as discussed above, a pressure/force marker or garage may be employed that provides an indication to the amount of spreading force achieved. For instance, FIG. 4B generically illustrates a pressure gauge (480) that may be employed. The pressure gauge (480) generically depicts some form of distance markers that can be etched or mounted on the surface of the support plate (310) or otherwise provided on a separate marking element that is connected to the base plate (310), providing a plurality of markers, P0, P1, P2, P3, etc., that are indicators of an amount of spreading force applied based on the spreading distance S achieved.

In particular, the marking P0 represents an initial state in which the contacting surface of the movable plate (340) is in an initial position (distance G from the first fixed plate (320)) with no force applied to the movable plate (340). As the movable plate (340) is pushed towards the second fixed plate (330), an amount of spreading force applied by the tool being tested can be determined as the contact surface of the movable plate (340) reaches each subsequent marker, P1, P2, P3, etc.

For instance, assuming that the testing device (400) of FIG. 4B is configured such that the springs (450) provides a total spring force of 10,000 psi, each marker P1, P2, P3, for example, can represent increased increments of 2500 psi, wherein marker P1 represents 2500 psi, marker P2 represents 5000 psi, and marker P3 represents 7500 psi. In this manner while a hydraulic tool is being tested, as the movable plate (340) reaches a given marker (P1, P2, P3) etc), the individual testing the tool can have some indication as to the amount of spreading force the tool is providing at that time.

Figure 5A:
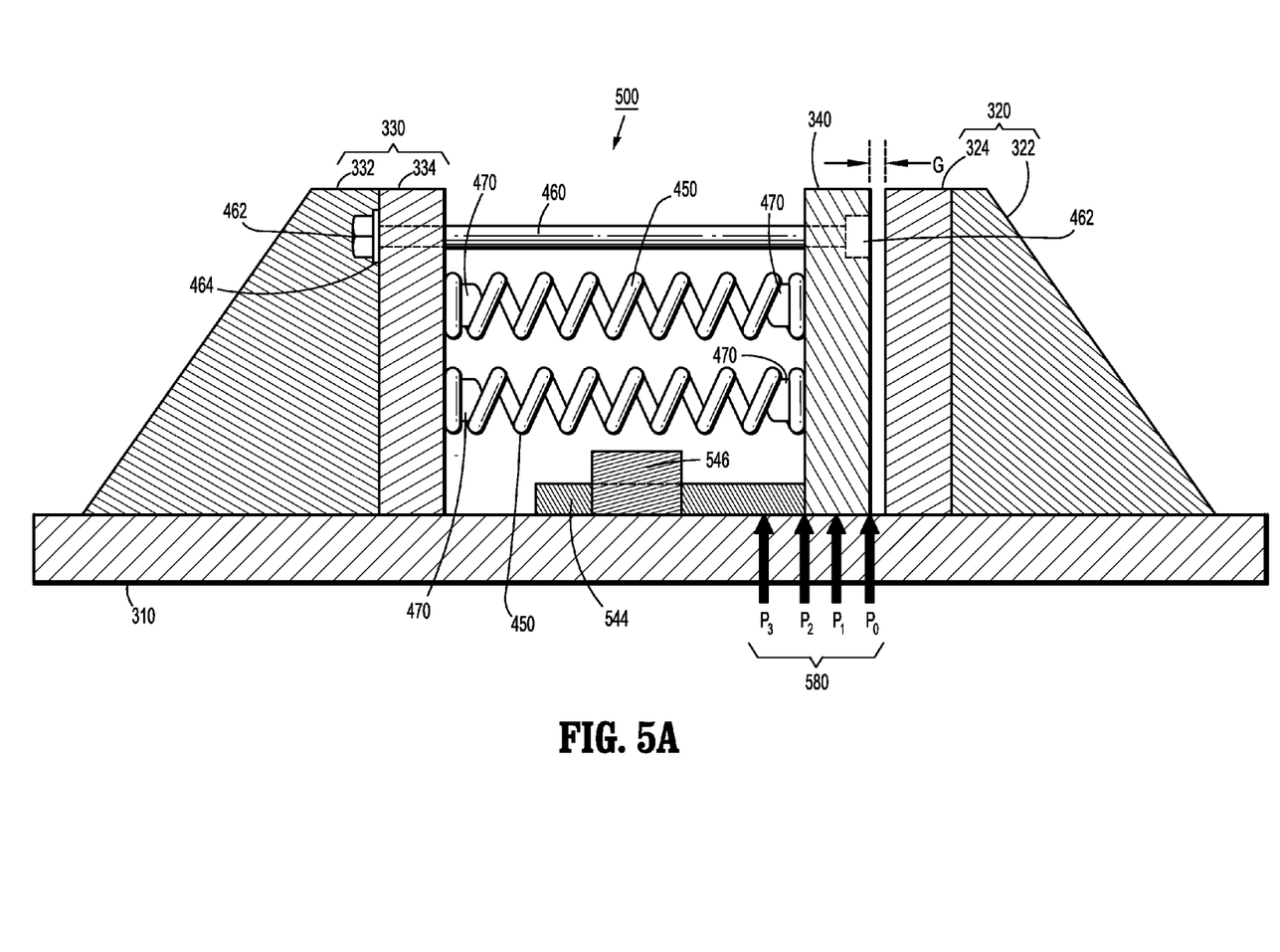
FIGS. 5A and 5B are a side schematic view and perspective view, respectively, of a device for testing and maintaining a hydraulic tool, according to another exemplary embodiment of the invention.
Figure 5B:
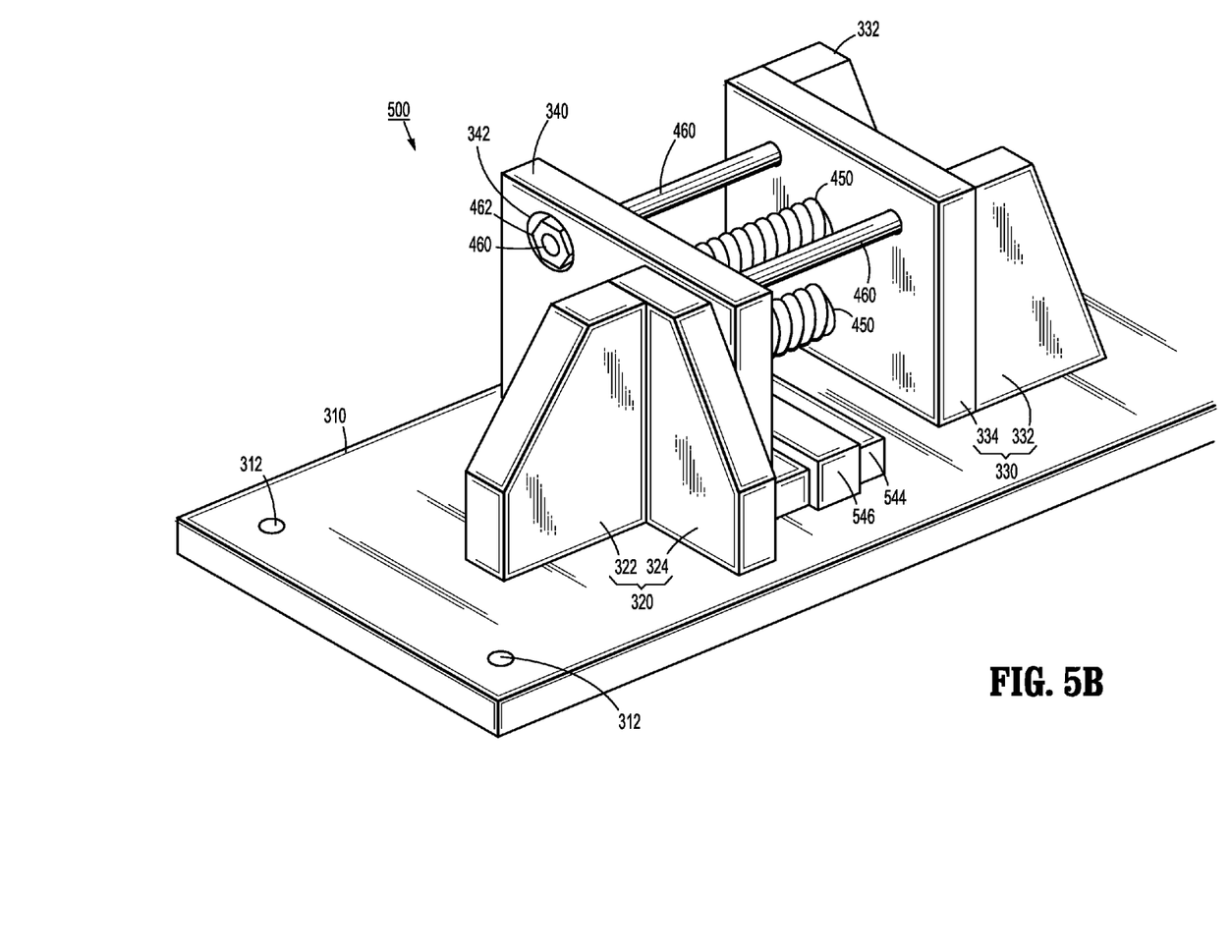

FIGS. 5A and 5B are schematic views of a device for testing and maintaining a hydraulic tool, according to another exemplary embodiment of the invention. In particular, FIG. 5A is a side schematic view of another embodiment of a test device (500) for testing and maintaining a hydraulic tool and FIG. 5B is a perspective view of the test device (500). The test device (500) shown in FIGS. 5A and 5B is similar to the test device (400) of FIGS. 4A/4B in that the test device (500) includes a support base (310), a first fixed plate (320), a second fixed plate (330), a movable plate (340), and a plurality of separate springs (450) and bolts (or rods) (460) disposed between the movable plate (340) and the second fixed plate (320). Moreover, similar to FIGS. 4A/4B, in the test device (500) of FIGS. 5A/5B, the springs (450) are held in place between the movable plate (340) and the flat plate portion (334) of the second fixed plate (330) using a plurality of metallic studs (470) that are fixedly connected (e.g., welded) to facing surfaces of the movable plate (340) and the flat plate portion (334) of the second fixed plate (330).

Furthermore, the test device (500) comprises a lower plate element (544) and a bracket element (546), wherein the lower plate element (544) slidably engages the bracket element (546). The lower plate element (544) is connected to the movable plate element (340). In one embodiment as specifically shown in FIG. 5B, the bracket element (546) is u-shaped bracket element which is welded to the base plate (310). The u-shaped bracket element (546) insertably receives the lower plate element (544). The collective structure of the lower plate element (544) and bracket element (546) serves various purposes. For example, the lower plate element (544) and bracket element (546) collectively serve as a means to stabilize the movable plate (340) as it slides back and forth.

Moreover, since the lower plate element (544) is connected to the movable plate 340, the lower plate element (544) and bracket element (546) collectively serve as a means to hold the assembly of components (e.g., plate (340), springs (450), rods (460)) together in place on the base plate (310). Indeed, FIG. 5B shows an initial state in which the contacting surface of the movable plate (340) is in an initial position (represented by marking P0) at a distance CG from the first fixed plate (320)) with no force applied to the movable plate (340). In this initial state, the lower plate element (544) is extended through the u-shaped bracket element (546), and thus, the assembly of components (544, 340, 450 and 460) are held in place in the test device (500) against the base plate (310).

Furthermore, the lower plate element (544) and bracket element (546) collectively serve as a stopping means to limit the amount of distance that the movable plate (340) can be pushed towards the second fixed plate (330) (so as to not over exert the compression springs (450)). Indeed, in one embodiment of the invention, the bracket element (546) can be positioned on the base plate (310) such that it serves as a stop element that makes contact to the movable plate (340) as the movable plate (340) is pushed towards the second fixed plate (330) with sufficient spreading force while using the test device (500) is being used. In another embodiment, the lower plate 544 can be sized (in length) so that it serve as a stop element when it makes contact against the fixed plate element (344) as the movable plate (340) is pushed towards the second fixed plate (330) with sufficient spreading force while the test device (500) is being used.

In the embodiment shown in FIGS. 4A and 4B, a lair of upper and lower rods (460) are implemented to provide added stability and support to the overall test device assembly (500). In the embodiment of FIGS. 5A and 5B, the pair of lower rod elements (460) may be eliminated, as the lower plate element (544) and the bracket element (546) provide added support and stability to the overall assembly, as discussed above, in an alternative embodiment, the upper and lower pairs of rods may be implemented together with the lower plate element (544) and the bracket element (546) provide even further support and stability to the overall test device assembly (500).

Figure 6A:
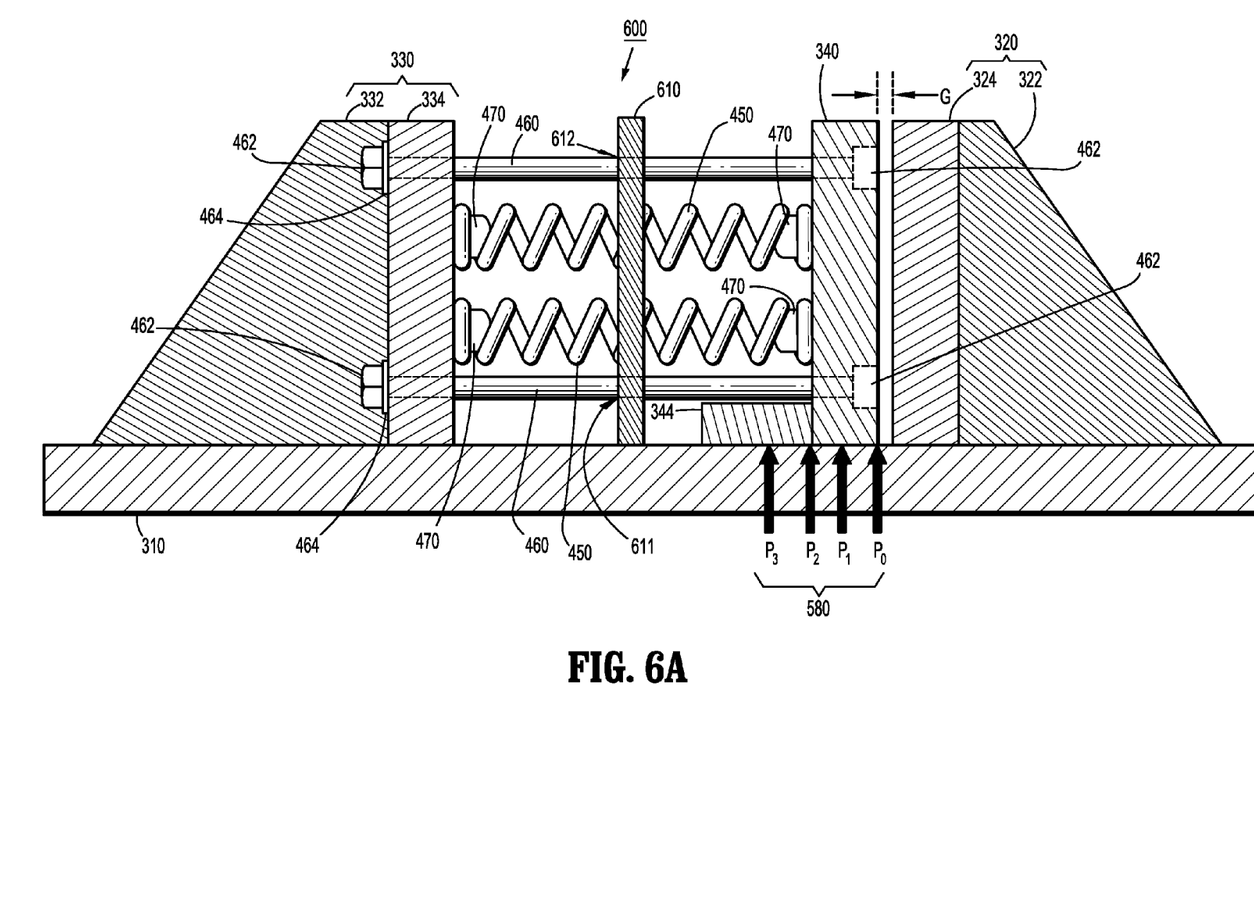
FIGS. 6A and 6B are a side schematic view and perspective view, respectively of a device for testing and maintaining a hydraulic tool, according to another exemplary embodiment of the invention.
Figure 6B:
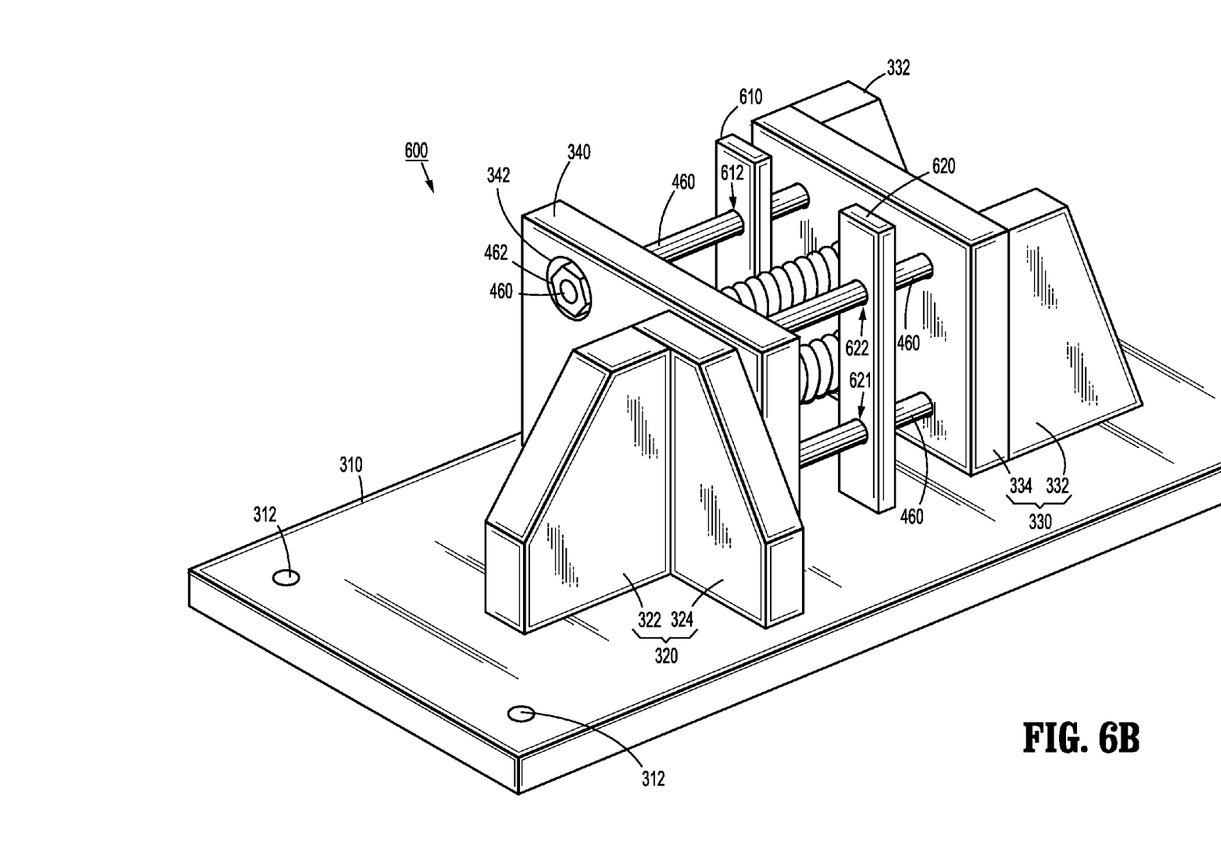

FIGS. 6A and 6B are schematic views of a device for testing and maintaining a hydraulic tool, according to another exemplary embodiment of the invention. In particular, FIG. 6A is a side schematic view of another embodiment of a test device (600) for testing and maintaining a hydraulic tool and FIG. 6B is a perspective view of the test device (600). The test device (600) shown in FIGS. 6A and 6B is similar to the test device (400) of FIGS. 4A/4B in that the test device (600) includes a support base (310), a first fixed plate (320), a second fixed plate (330), a movable plate (340), and a plurality of separate springs (450) and bolts (or rods) (460) disposed between the movable plate (340) and the second fixed plate (320). Moreover, similar to FIGS. 4A/4B, in the test device (600) of FIGS. 6A/6B, the springs (450) are held in place between the movable plate (340) and the flat plate portion (334) of the second fixed plate (330) using a plurality of metallic studs (470) that are fixedly connected (e.g., welded) to facing surfaces of the movable plate 340) and the flat plate portion (334) of the second fixed plate (330).

Furthermore, as shown in FIGS. 6A and 6B, the test device (600) comprises a first rod support element (610) and a second rod support element (620), which are fixedly connected (e.g., welded) to the base plate (310). The first rod support element (610) comprises a first aperture (611) and a second aperture (612) which insertably receive the lower and upper rods (460), respectively, on one side of the device (600). The second rod support element (620) comprises a first aperture (621) and a second aperture (622) winch insertably receive the lower and upper rods (460), respectively, on the other side of the test device (600). The first and second rod support elements (610) and (620) serve various purposes.

For example, the first and second rod support elements (610) and (620) collectively serve as a means to stabilize the overall assembly and hold the rods (460) in vertical position with regard to the base plate (310). While the apertures (611, 612, 621 and 622) of the first and second rod support elements (610) and (620) are sized to allow the rods (460) to freely slide back and forth there through, the first and second rod support elements (610) and (620) maintain the vertical position of the rods (460) in relation to the base plate (310), which, in turn, maintains the movable plate (340) springs (450) in place in the overall test device assembly (600).

Furthermore, the first and second rod support elements (610) and (620) may collectively serve as a stopping means to limit the amount of distance that the movable plate (340) can be pushed towards the second fixed plate (330) (so as to not over exert the compression springs (450)). Indeed, in one embodiment of the invention, the first and second rod support elements (610) and (620) can be positioned on the base plate (310) such that they act as stop elements that make contact with the movable plate (340) as the movable plate (340) is pushed towards the second fixed plate (330) with sufficient spreading force while the test device (600) is being used.

Figure 7A:
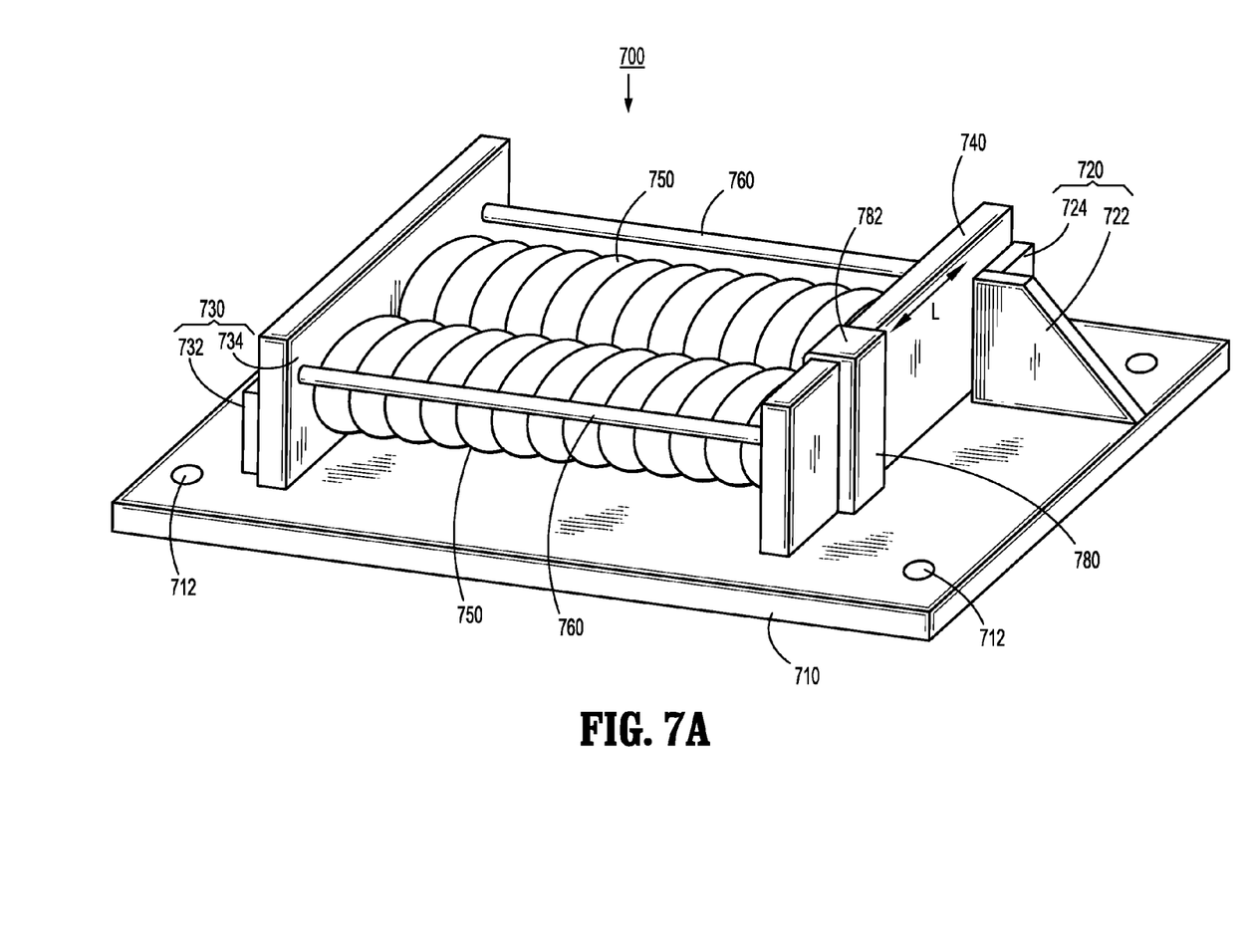
FIGS. 7A and 7B are perspective views of a device for testing and maintaining a hydraulic tool, according to another exemplary embodiment of the invention.
Figure 7B:
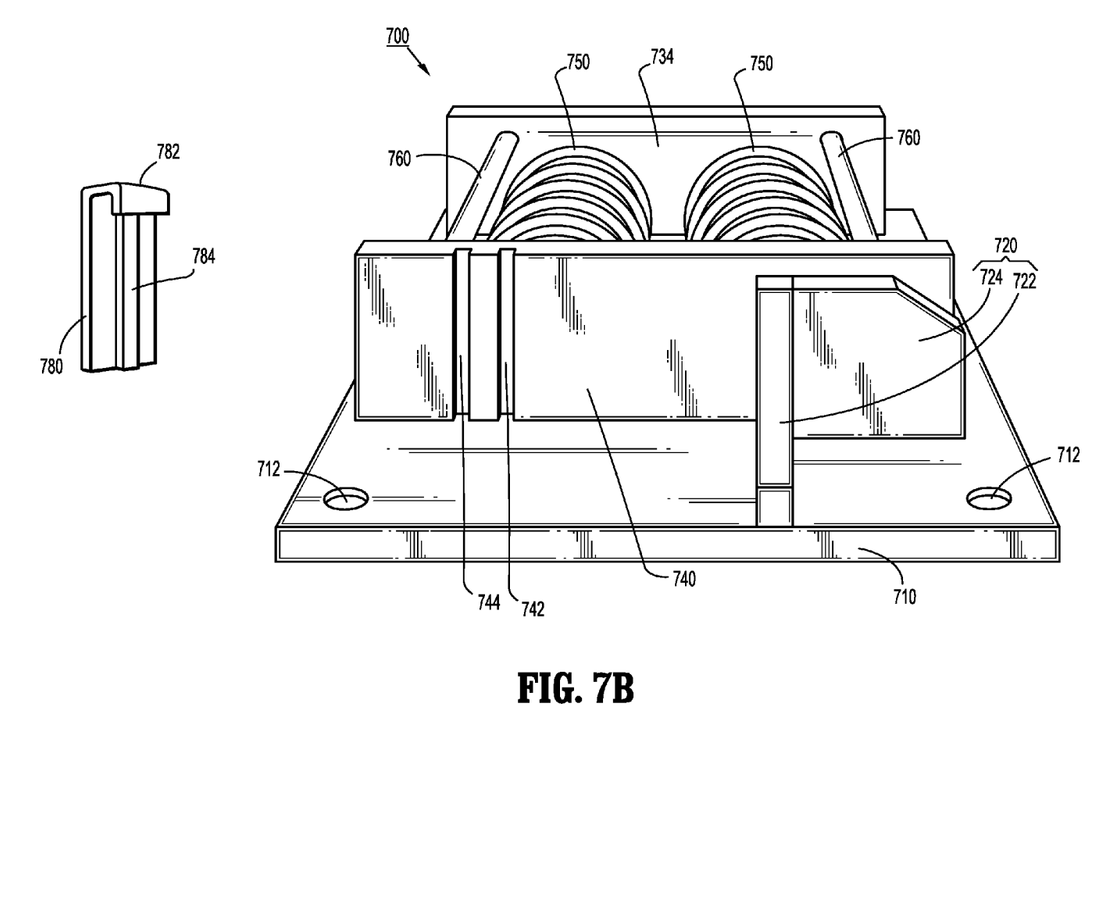

FIGS. 7A and 7B are perspective views of a device (700) for testing and maintaining, a hydraulic tool, according to another exemplary embodiment of the invention. In general, the test device (700) shown in FIGS. 7A and 7B is similar to previous embodiments in that the test device (700) includes a support base (710), a first fixed plate (720), a second fixed plate (730), a movable plate (740), and a plurality of separate springs (750) and bobs (or rods) (760) disposed between the movable plate (740) and the second fixed plate (730). The first fixed plate (720) comprises a first member (722) and a second member (724) which form a right angle (90 degrees) fixed plate structure. The second fixed plate (730) comprises a first member (734) that is disposed parallel to the movable plate (740), and one or more extended support members (732) are disposed perpendicular to the first member (734) to provide support for compressive forces that are applied to the second fixed plate (730). The supporting base plate (710) may comprise a plurality of thru-holes (712) formed in corner regions of the base plate (710) so that the test device (700) can be bolted or screwed down to a supporting work bench structure, for example.

Moreover, the springs (750) are held in place between the movable plate (740) and the flat plate portion (734) of the second fixed plate (730) using a plurality of metallic studs (not specifically shown) that are fixedly connected (e.g., welded) to lacing surfaces of the movable, plate (740) and the flat plate portion (734) of the second fixed plate (730), as discussed above. In the embodiment of FIGS. 7A and 7B, one end of each guiding rod (760) is welded to a surface of the movable plate (740), while the opposite end of each guiding rod (760) slidably engages the first member (734) of the second fixed plate (730) and is held in place with movable nuts that can be turned, which enables adjustment of the initial gap G between the movable plate (740) and the second member (724) of the first fixed plate (720).

As further shown in FIGS. 7A and 7B, the test device (700) further comprises a stop member (780) that is removably coupled to the movable plate (740). The stop member (780) comprises a first retaining member (782) and a second retaining member (784), which serve to retain the stop member (780) in position on a front side of the movable plate (740). The movable plate (740) comprises a plurality of slots (742) and (744), which interface with the second retaining member (784) on the backside of the stopper member (780). The first retaining member (782) is a clip-type element that wraps around a top-side edge of the moveable plate (740) to maintain the stop element (780) against the front-side surface of the movable plate (740), while the second retaining member (784) (groove) and the slots (742) and (744) (tongue) provide a "tongue and groove" connection that holds the stop member (780) in place at some position on the front-side of the movable plate (740), such as specifically shown in FIG. 7A.

With the stop element (780) in position, there is a distance "L" between an inner surface of the stop element (780) and an inner surface of the member (722) of the first fixed plate (720). This distance "L" is adjusted depending on which slot (742) or (744) is used to engage the second retaining member (784) (groove) of the stop element (780). The slots (742) and (744) are formed in the surface of the movable plate (740) in a spaced relation to the position of the fixed plate (720) so that the distance "L" can be selected, to accommodate standard sizes of jaw members of different commercially available hydraulic forcible entry tools that can be used with the device (700).

For example, when using the hydraulic, forcible entry tool (10) of FIGS. 1A and 1B with test device (700) in FIG. 7A, with the tool (10) in a non-extended position (as shown in FIG. 1A), the hydraulic forcible entry tool (10) would be initially positioned with the sharp blade tip (18C) inserted in the initial gap between the movable plate (740) and the fixed plate (720) and the top edge (18D) of the movable jaw member (18B) would be positioned adjacent to the inner side surface of the stop element (780). As the hydraulic forcible entry tool (10) is actuated (as shown in FIG. 1B) with the piston (19) in an extended position, the beveled tip of the fixed jaw (18A) would be pressed against the inside edge of the first fixed plate (720) and the movable jaw (18B) would be pressed against the surface of the movable plate (740). Under high compressive forces, there may be tendency for the fixed jaw (18A) to accidently be disengaged from the fixed plate member (720) due to, e.g., the beveled tip of the fixed jaw (18A). However, by use of the stop element (780), the top edge (18D) of the movable jaw (18B) would be pressed up against the inside edge of the stop element (780), thereby preventing the tool (10) from accidently disengaging the test device (700) under high compressive forces, which would cause the movable plate (740) to snap back into position, and possibly cause injury to the individual operating the test device (700). The stop element (780) provides a fixed distance "L" that corresponds to the dimensions of the jaw element (18) so as to prevent the tool (10) from accidently disengaging the test device (700) during a test operation.

Although FIG. 7B illustrates two slots, (742) and (744), the movable plate (740) can be formed with three or more slots to accommodate the blade dimensions of other standard hydraulic forcible entry tools. Moreover, in embodiments where the test device (700) is designed for a specific standard hydraulic forcible entry tool requiring no adjustment of the distance "L" between an inner surface of the stop element (780) and an inner surface of the member (722), the stop element (780) can be fixedly mounted to the front-side surface of the movable plate (740) by e.g., welding. With the test device COO embodiment shown in FIGS. 7A and 7B, the device is formed with a wider profile (e.g., wider movable plate (740) and element (734)) which enables use of the stop element (780) with adjustable positions for various commercially available tools. The wider profile enables the multiple springs (750) to be laterally positioned side by side, which also enables a reduction in the vertical profile of the test device (700).

The exemplary test devices described herein provide inexpensive designs that can be used to test and maintain hydraulic tools such as hydraulic forcible entry tools, without the need for complex or expensive test equipment. Test devices according to exemplary embodiments of the invention made of steel structures and strong, durable compression springs can provide significant durability for long lasting use for testing and maintaining hydraulic tools.

Although illustrative embodiments of the present invention have been described herein with reference to the accompanying drawings, it is to be understood that the invention is not limited to those embodiments, and that various other changes and modifications may be affected therein by one skilled in the art without departing from the scope or spirit of the invention.

I claim:

1. A device for testing a hydraulic tool, comprising:
   a support base;
   a first fixed plate fixedly connected to the support base;
   a second fixed plate fixedly connected to the support base;
   a movable plate, disposed between the first and second fixed plate; and
   one or more compression springs disposed between the movable plate and the second fixed plate,
   wherein the movable plate and the first fixed plate are oriented with respect to each other and adapted to engage a hydraulic tool being tested, and wherein the movable plate is adapted to be moved towards the second fixed plate upon actuation of the hydraulic tool and compress the one or more compression springs to provide a compression force that provides a test load for testing the hydraulic tool.

2. The device of claim 1, wherein the first fixed plate comprises a first member and a second member, which form a right angle fixed plate structure.

3. The device of claim 1, wherein second fixed plate comprises a first member that is disposed parallel, to the movable plate, and a plurality of extended support members that are disposed perpendicular to the first member to provide support for compressive forces that are applied to the second fixed plate as the movable plate is pushed towards the second fixed plate.

4. The device of claim 1, further comprising, a force indicator element that indicates an amount of spreading, force applied by the hydraulic tool based on a distance that the movable plate is moved towards the second fixed plate.

5. The device of claim 1, wherein the support base, first fixed plate, second fixed plate, and movable plate are formed of pieces of planar steel having a thickness of about ½ inch.

6. The device of claim 1, wherein each of the one or more compression springs are held in place between the movable plate and the second fixed plate with a rod element that longitudinally extends within an interior of the compression spring.

7. The device of claim 6, wherein one end of each rod is fixedly attached to the movable plate, and wherein another end of each rod slidably extends through a hole formed in portion of the second fixed plate.

8. The device of claim 1, wherein each of the one or more compression springs are held in place between the movable plate and the second fixed plate using metallic studs that are fixedly connected to facing surfaces of the movable plate and the second fixed plate.

9. The device of claim 8, wherein the studs are dimensioned to snuggly fit within the inner region of the one or more compression springs.

* * * * *